(12) United States Patent
Kruecker et al.

(10) Patent No.: US 12,193,871 B2
(45) Date of Patent: Jan. 14, 2025

(54) TEMPORAL MAPPING OF THERMAL ABLATION AREAS

(71) Applicant: KONINKLIJKE PHILIPS N.V., Eindhoven (NL)

(72) Inventors: Jochen Kruecker, Andover, MA (US); Shriram Sethuraman, Lexington, MA (US); Faik Can Meral, Mansfiled, MA (US); William Tao Shi, Wakefield, MA (US); Evgeniy Leyvi, Arlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 764 days.

(21) Appl. No.: 17/295,462

(22) PCT Filed: Nov. 15, 2019

(86) PCT No.: PCT/EP2019/081450
§ 371 (c)(1),
(2) Date: May 20, 2021

(87) PCT Pub. No.: WO2020/104308
PCT Pub. Date: May 28, 2020

(65) Prior Publication Data
US 2021/0401397 A1 Dec. 30, 2021

Related U.S. Application Data

(60) Provisional application No. 62/769,602, filed on Nov. 20, 2018.

(51) Int. Cl.
*A61B 8/08* (2006.01)
*A61B 18/00* (2006.01)
(Continued)

(52) U.S. Cl.
CPC ............ *A61B 8/0841* (2013.01); *A61B 8/085* (2013.01); *A61B 8/485* (2013.01); *A61B 18/00* (2013.01);
(Continued)

(58) Field of Classification Search
CPC ....... A61B 8/0841; A61B 8/085; A61B 8/485; A61B 34/10; A61B 2034/104; A61B 18/00; A61B 2018/00577; G06V 10/26
See application file for complete search history.

(56) References Cited

U.S. PATENT DOCUMENTS 9,277,970 B2   3/2016 Mansi
2007/0112342 A1   5/2007 Pearson
(Continued)

FOREIGN PATENT DOCUMENTS

DE   102011075738 A1   11/2012
EP   2640292 A1   9/2013
(Continued)

OTHER PUBLICATIONS

PCT International Search Report, International application No. PCT/EP2019/081450, Feb. 4, 2020.

*Primary Examiner* — Chao Sheng
(74) *Attorney, Agent, or Firm* — Sherry Austin

(57) ABSTRACT

Various embodiments of the present disclosure include a thermal ablation probabilistic controller (30) employing an ablation probability model (32) trained to render a pixel ablation probability for each pixel of an ablation scan image illustrative of a static anatomical ablation. In operation, the thermal ablation probabilistic controller (30) spatially aligns a temporal sequence of ablation scan datasets representative of a dynamic anatomical ablation, and applies the ablation probability model (32) to the spatial alignment of the temporal sequence of ablation scan datasets to render the (Continued)

pixel ablation probability for each pixel of the ablation scan image illustrative of the static anatomical ablation.

20 Claims, 10 Drawing Sheets

(51) Int. Cl.
 *A61B 34/10* (2016.01)
 *G06V 10/26* (2022.01)
(52) U.S. Cl.
 CPC .... *A61B 34/10* (2016.02); *A61B 2018/00577* (2013.01); *A61B 2034/104* (2016.02); *G06V 10/26* (2022.01)

(56) References Cited

U.S. PATENT DOCUMENTS

| | | |
|---|---|---|
| 2008/0033419 A1 | 2/2008 | Nields |
| 2014/0058387 A1* | 2/2014 | Kruecker .............. G16H 50/50 606/41 |
| 2015/0272653 A1 | 10/2015 | Brunke |
| 2016/0131540 A1 | 5/2016 | Anand |
| 2018/0221075 A1 | 8/2018 | Warner |

FOREIGN PATENT DOCUMENTS

| | | |
|---|---|---|
| WO | WO2012066449 A1 | 5/2012 |
| WO | WO2016156540 A1 | 10/2016 |
| WO | WO2018092071 A1 | 5/2018 |
| WO | WO2018130976 A1 | 7/2018 |

* cited by examiner

TEMPORAL MAPPING OF THERMAL ABLATION AREAS

CROSS-REFERENCE TO RELATED APPLICATIONS

This patent application claims the priority benefit under 35 U.S.C. § 371 of International Patent Application no. PCT/EP2019/081450, filed Nov. 15, 2019, which claims the benefit of U.S. Application Ser. No. 62/769,602, filed on Nov. 20, 2018. These applications are hereby incorporated by reference herein in their entirety.

FIELD OF THE INVENTION

The present disclosure generally relates to percutaneous thermal ablation. The present disclosure specifically relates to imaging of thermal ablation areas for monitoring the percutaneous thermal ablation.

BACKGROUND OF THE INVENTION

Percutaneous thermal ablation is a widely used tool in the interventional radiologist's arsenal of anti-cancer therapies, with about 200,000 procedures performed worldwide in 2016, and a growth rate of over 8%. For precise ablation of tumors, while sparing healthy tissue nearby, monitoring of the ablation procedure is required (i.e., visualization of the growing thermal ablation area(s)). Ultrasound imaging is commonly used to guide needle placement for ablations, but current ultrasound-based methods for monitoring may involve an inadequate monitoring and intra-procedural assessment of ablations that may lead to incomplete ablation of the tumor resulting in tumor recurrence, or potential damage to healthy critical structures near the ablation area(s).

More particularly, ultrasound-based methods for ablation monitoring have been researched and shown that these methods are promising for depicting the ablation boundary (e.g., shear-wave elastography). However, a difficult imaging situation during ablation may lead to significant artifacts and/or low signal-to-noise (SNR) ratio, such as, for example, a presence of the ablation electrode, tumor, and thermal gradient, in addition to common tissue inhomogeneities and physiological motion that may lead to significant artifacts and/or low SNR ratio.

Of importance is, the relevant margins to be observed in ablation monitoring are the contours of the area(s) with irreversible, permanent thermal tissue damage due to coagulation necrosis. The coagulation process is marked by a significant increase in tissue stiffness. During the ablation procedure, the coagulation zone will grow from the area immediately around the ablation electrode tip to a distance of several centimeters from the tip. Since ablation monitoring images may be fraught with artifacts and low SNR, it may become difficult to discern the relevant boundary of the ablation in individual images at discrete time points. Therefore, when looking at such individual images, the contours of an ablation area are difficult to identify, which may lead to incomplete ablations, tumor recurrence, or damage to healthy critical structures.

SUMMARY OF THE INVENTION

While known ultrasound-based methods for ablation monitoring have proven to be beneficial (e.g., shear-wave elastography), there remains a need for improved techniques for providing accurate and reliable monitoring of ablation area(s) via scan imaging of an ablated anatomical region. The present disclosure teaches a probabilistic approach to identify ablation area(s) based on the observation and tracking of individual ablation monitoring images.

More particularly, for purposes of the description and claims of the present disclosure, a scan image of an unchanging anatomical ablation at a discrete time is deemed a static anatomical ablation, and a temporal sequence of scan images of an enlarging anatomical ablation over a period of time is deemed a dynamic anatomical ablation. The present disclosure teaches a probabilistic approach to identify ablation area(s) of a static anatomical ablation based on the observation and tracking of a dynamic anatomical ablation.

One embodiment of the present disclosure is a thermal ablation probabilistic controller employing a memory including an ablation probability model trained to render a pixel ablation probability for each pixel of an ablation scan image illustrative of a static anatomical ablation (i.e., an unchanging anatomical ablation at a discrete time).

The thermal ablation probabilistic controller further employs one or more processors for spatially aligning a temporal sequence of ablation scan datasets representative of a dynamic anatomical ablation (i.e., an enlarging anatomical ablation over a period of time), and applying the ablation probability model to the spatial alignment of the temporal sequence of ablation scan datasets to render the pixel ablation probability for each pixel of the ablation scan image illustrative of the static anatomical ablation.

A second embodiment of the present disclosure is a non-transitory machine-readable storage medium encoded with instructions for execution by one or more processors of an ablation probability model trained to render a pixel ablation probability for each pixel of an ablation scan dataset representative of a static anatomical ablation (i.e., an unchanging anatomical ablation at a discrete time).

The non-transitory machine-readable storage medium comprises instructions to spatially align a temporal sequence of ablation scan datasets representative of a dynamic anatomical ablation (i.e., an enlarging anatomical ablation over a period of time), and to apply the ablation probability model to the spatial alignment of the temporal sequence of ablation scan datasets to render the pixel ablation probability for each pixel of the ablation scan image illustrative of the static anatomical ablation.

A third embodiment of the present disclosure is a thermal ablation probabilistic method executable by a thermal ablation probabilistic controller including an ablation probability model trained to render a pixel ablation probability for each pixel of an ablation scan dataset representative of a static anatomical ablation (i.e., an unchanging anatomical ablation at a discrete time).

The thermal ablation probabilistic method involves a spatial alignment, by the thermal ablation probabilistic controller, of a temporal sequence of ablation scan dataset representative of a dynamic anatomical ablation (i.e., an enlarging anatomical ablation over a period of time).

The thermal ablation probabilistic method further involves an application, by the thermal ablation probabilistic controller, of the ablation probability model to the spatial alignment of the temporal sequence of ablation scan dataset to render the pixel ablation probability for each pixel of the ablation scan image illustrative of the static anatomical ablation.

For various embodiments of the present disclosure, the application of the ablation probability model to the spatial alignment of the temporal sequence of ablation scan dataset may involve a temporal pixel intensity of a pixel of the ablation scan image illustrative of the static anatomical ablation being derived from the spatial alignment of the temporal sequence of ablation scan image data.

Additionally, the application of the ablation probability model to the spatial alignment of the temporal sequence of ablation scan dataset may further involve a temporal pixel intensity of one or more neighboring pixels of the ablation scan image illustrative of the static anatomical ablation being derived from the spatial alignment of the temporal sequence of ablation scan dataset.

Furthermore, the application of the ablation probability model to the spatial alignment of the temporal sequence of ablation scan dataset may further involve an ablation probability rule being applied to the temporal pixel intensities of the pixel and the neighboring pixel(s) to render the pixel ablation probability of the pixel.

For various embodiments of the present disclosure, the application of the ablation probability model to the spatial alignment of the temporal sequence of ablation scan dataset may involve a temporal pixel intensity valuation by the ablation probability model of a temporal sequence of each pixel of the spatial alignment of the temporal sequence of ablation scan image data.

Additionally, the application of the ablation probability model to the spatial alignment of the temporal sequence of ablation scan dataset may further involve a spatial pixel intensity assessment by the ablation probability model of the temporal pixel intensity valuation of one or more neighboring pixels of the spatially alignment of the temporal sequence of ablation scan image data Furthermore, the application of the ablation probability model to the spatial alignment of the temporal sequence of ablation scan dataset may further involve an application of one or more ablation probability rules to the temporal pixel intensity valuation and the spatial pixel intensity assessment. The ablation probability rule(s) are based on a comparison of the temporal pixel intensity valuations of the pixel and the neighboring pixel(s) to an ablation threshold.

For embodiments of the present disclosure, an ablation probability image derived from the pixel ablation probability for each pixel of the ablation scan image illustrative of the static anatomical ablation may be generated and communicated (e.g., a display and/or a printing of a black and white or greyscale or color-coded image of probable ablation area(s) of an ablated anatomical region).

Alternatively or concurrently, an ablation probability anatomical scan image is derived from an anatomical image of the static anatomical ablation and further derived from the pixel ablation probability for each pixel of the ablation scan image illustrative of the static anatomical ablation may be generated and communicated (e.g., a display and/or a printing of an overlay of probable ablation area(s) on an anatomical scan image of an ablated anatomical region).

Alternatively or concurrently, an ablation probability ablation scan image derived from the ablation scan image illustrative of the static anatomical ablation and further derived from the pixel ablation probability for each pixel of the ablation scan image illustrative of the static anatomical ablation may be generated and communicated (e.g., a display and/or a printing of an overlay of probable ablation area(s) on an ablation ultrasound scan image displayed and/or printed).

For purposes of the description and claims of the present disclosure:

(1) terms of the art including, but not limited to, "scan", "ablation", "static anatomical ablation", "dynamic anatomical ablation", "pixel", "dataset", "spatial alignment" and "probabilistic model" are to be interpreted as known in the art of the present disclosure and as exemplary described in the present disclosure;

(2) more particularly, the term "pixel" encompasses both a planar pixel and a volumetric pixel (aka, a voxel);

(3) the term "controller" broadly encompasses all structural configurations, as understood in the art of the present disclosure and as exemplary described in the present disclosure, of main circuit board or integrated circuit for controlling an application of various inventive principles of the present disclosure as exemplary described in the present disclosure. The structural configuration of the controller may include, but is not limited to, processor(s), computer-usable/computer readable storage medium(s), an operating system, application module(s), peripheral device controller(s), slot(s) and port(s). A controller may be housed within or linked to a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop or a tablet;

(4) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application; and (5) the term "data" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Data communication various components of the present disclosure may involve any communication method as known in the art of the present disclosure including, but not limited to, data transmission/reception over any type of wired or wireless datalink and a reading of data uploaded to a computer-usable/computer readable storage medium.

The foregoing embodiments and other embodiments of the inventions of the present disclosure as well as various structures and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

Figure 1:
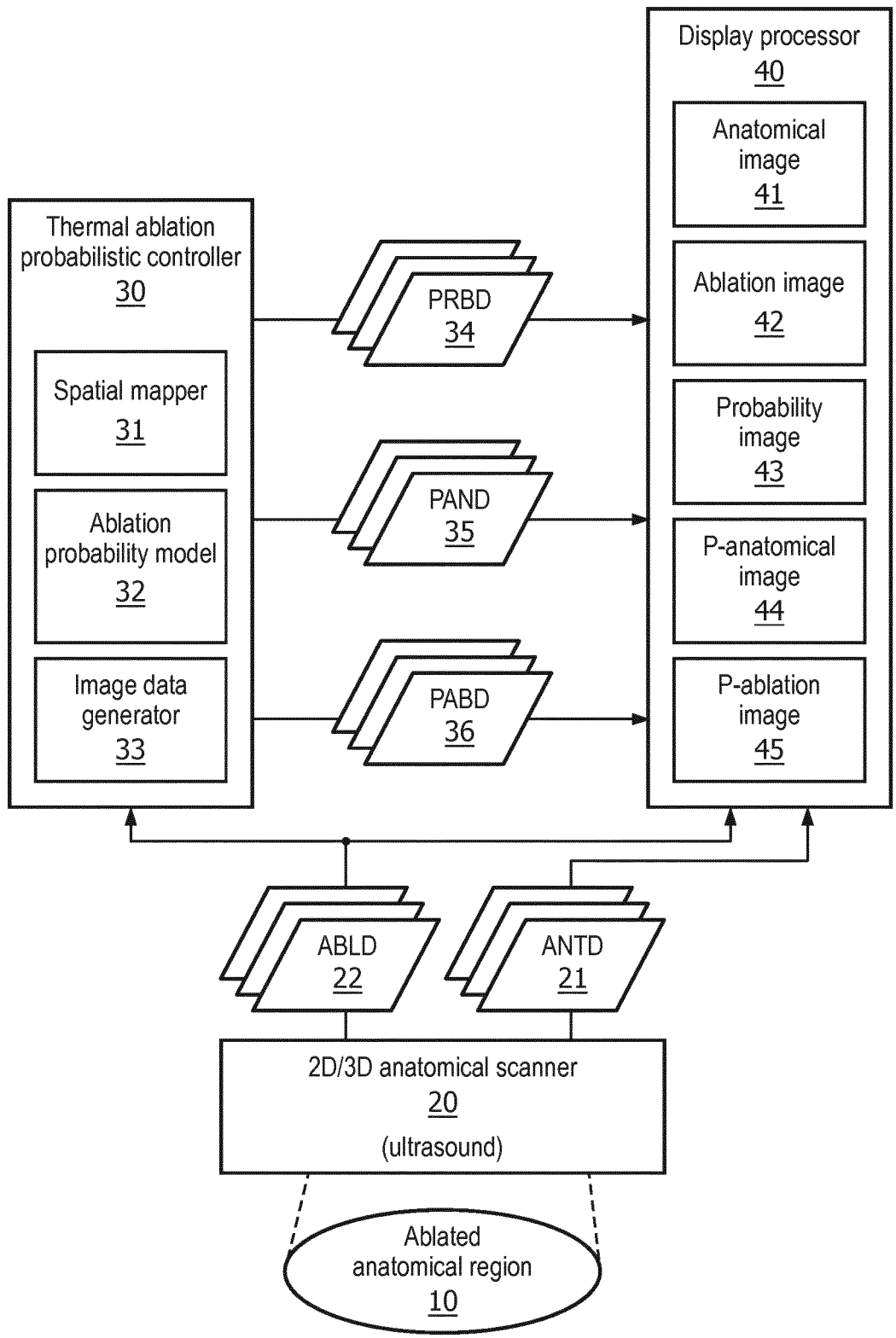
FIG. 1 illustrates an exemplary embodiment of a thermal ablation probabilistic system in accordance with various aspects of the present disclosure.
Figure 2:
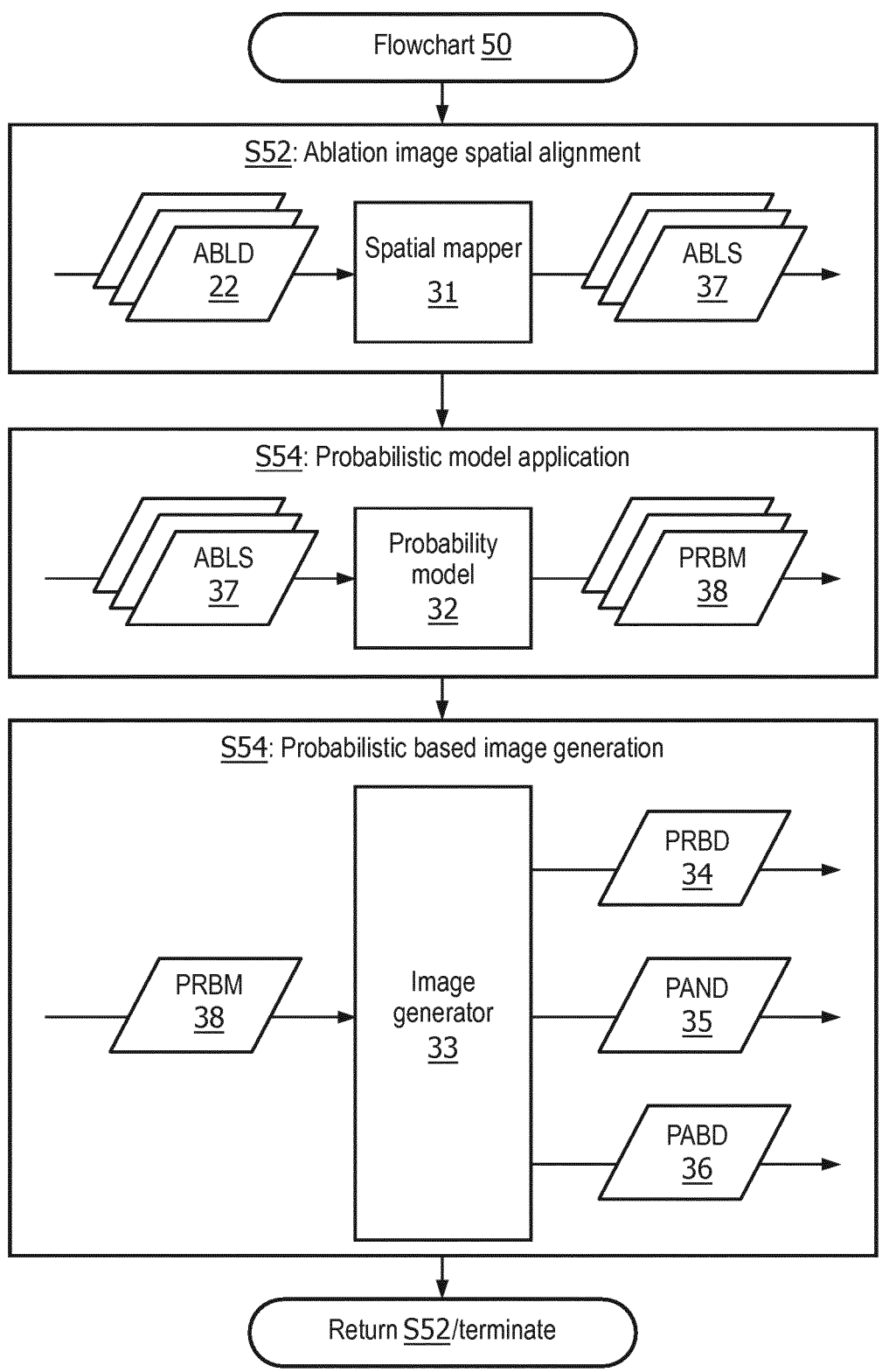
FIG. 2 illustrate an exemplary embodiment of a flowchart representative of a thermal ablation probabilistic method in accordance with various aspects of the present disclosure.

To facilitate an understanding of the various inventions of the present disclosure, the following description of FIGS. 1 and 2 teaches an exemplary thermal ablation probabilistic systems and methods of the present disclosure. From this description, those having ordinary skill in the art will appreciate how to apply the inventive principles of the present disclosure for making and using additional embodiments of thermal ablation probabilistic systems and methods of the present disclosure.

Referring to FIG. 1, a thermal ablation probabilistic system of the present disclosure employs an anatomical scanner 20 for scanning an ablated anatomical region 10 (e.g., a cranial region or a thoracic region) to generate two-dimensional ("2D") scan dataset of pixels representative of a static anatomical ablation of ablated anatomical region 10 and/or three-dimensional ("3D") scan dataset of volumetric pixels (aka, voxels) representative of the static anatomical ablation of ablated anatomical region 10.

More particularly, the generated 2D/3D scan dataset is representative of an unchanging anatomical ablation of ablated anatomical region 10 at a discrete time, which is deemed a static anatomical ablation. A temporal sequence of generated 2D/3D scan datasets is representative of an enlarging anatomical ablation over a period of time, which is deemed a dynamic anatomical ablation. In essence, a dynamic anatomical ablation consists of a temporal sequence of static anatomical ablations.

In practice, 2D/3D anatomical scanner 20 may be any type of anatomical scanner for visualizing feature(s) of ablation area(s) of ablated anatomical region 10 that distinguish the ablation area(s) from surrounding un-ablated area(s). Examples of such features include, but not limited to, tissue stiffness, tissue density and tissue temperature.

In one embodiment, 2D/3D anatomical scanner 20 is an ultrasound scanner for generating 2D or 3D anatomical scan dataset 21 representative of a scan image of the ablated anatomical region 10 excluding any type of a delineation of ablation area(s) (e.g., a B-mode ultrasound imaging). Alternatively or concurrently, the ultrasound scanner may generate 2D or 3D ablation scan dataset 22 representative of a scan image of the ablated anatomical region 10 including a delineation of ablation area(s) (e.g., ultrasound shear-wave elastography imaging). Examples of such anatomical scanners 20 include, but are not limited to, the ultrasound scanners incorporated within the Philips PercuNav systems and the Philips UroNav systems.

Still referring to FIG. 1, a thermal ablation probabilistic system of the present disclosure further employs a display processor 40 for generating an anatomical scan image 41 from a 2D/3D anatomical scan dataset 21 (e.g., a B-mode ultrasound imaging) of a static anatomical ablation or from a temporal sequence of 2D/3D anatomical scan datasets 21 (e.g., temporal B-mode ultrasound imaging) of a dynamic anatomical ablation. Alternatively or concurrently, display processor 40 may generate an ablation scan image 42 from a 2D/3D ablation scan dataset 22 (e.g., ultrasound shear-wave elastography imaging) of a static anatomical ablation or from a temporal sequence of 2D/3D ablation scan dataset 22 (e.g., temporal ultrasound shear-wave elastography imaging) of a dynamic anatomical ablation.

In practice, display processor may any type of display processor for converting pixels/voxels of a scan dataset into display pixels/voxels. Examples of such display processors include, but are not limited to, the display processors incorporated within the Philips PercuNav systems and the Philips UroNav systems.

Still referring to FIG. 1, a thermal ablation probabilistic system of the present disclosure further employs a thermal ablation probabilistic controller 30 of the present disclosure. To apply a probabilistic approach to identify ablation area(s) of a static anatomical ablation based on the observation and tracking of a dynamic anatomical ablation, thermal ablation probabilistic controller 30 includes application modules in the form of a spatial mapper 31, a ablation probability model 32 and an image data generator 33 for executing a thermal ablation probabilistic method of the present disclosure as represented by a flowchart 50 shown in FIG. 2.

Referring to FIG. 2, during a stage S52 of flowchart 50, spatial mapper 31 is configured to spatially align a temporal sequence of ablation scan datasets 22 to thereby spatially align a temporal pixel intensity of each pixel of the ablation scan datasets 22. Spatial mapper 31 is further configured to buffer a temporal sequence of spatially aligned ablation scan datasets 37.

Figure 3:
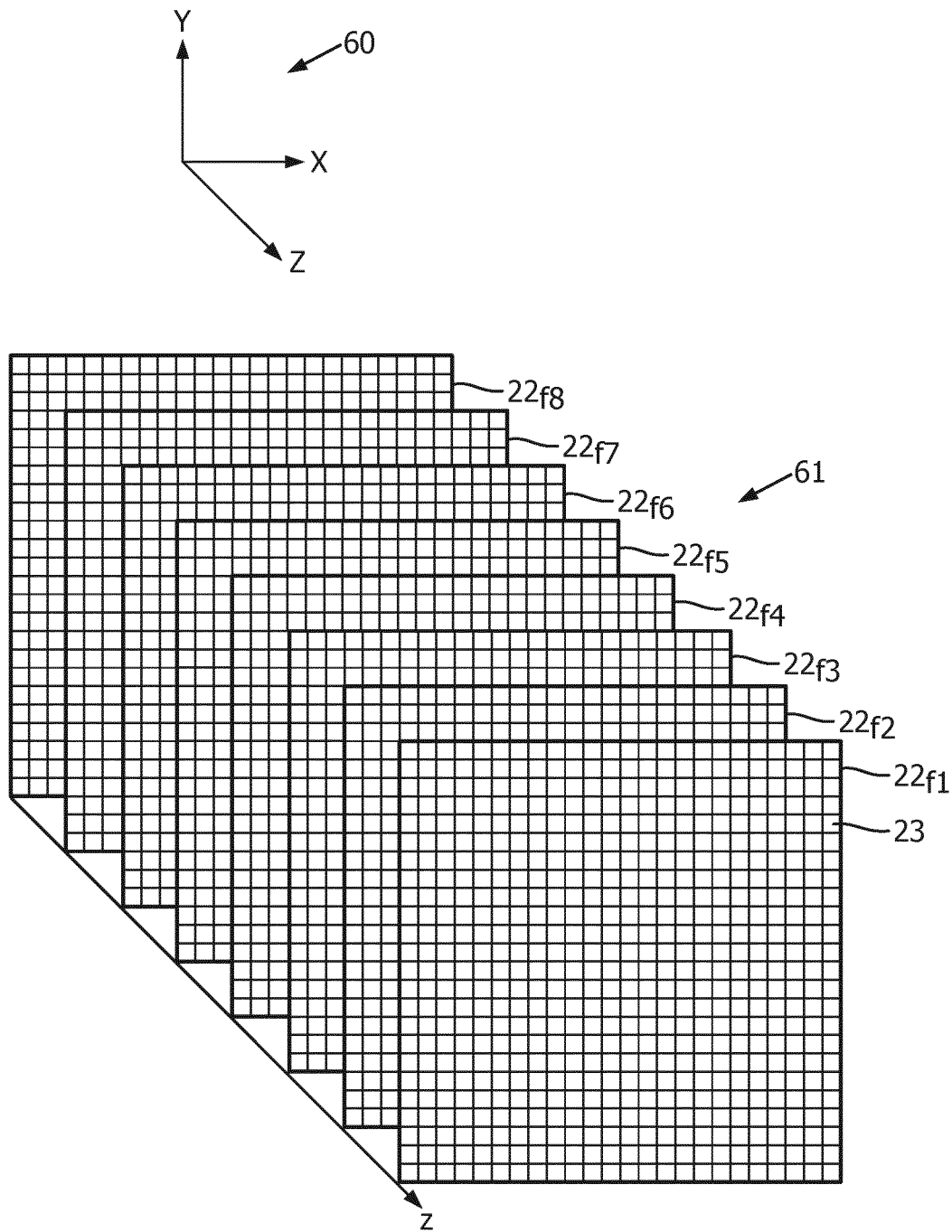
FIG. 3 illustrates an exemplary spatial alignment of a temporal sequence of ablation scan dataset in accordance with various aspects of the present disclosure.

For example, FIG. 3 illustrates a spatial alignment 61 of a temporal sequence of eight (8) ablation scan datasets $22_{f1}$-$22_{f8}$ along a Z-axis of a coordinate system 60 defined by a baseline ablation scan dataset, which may be the first ablation scan dataset $22_{f1}$ of the temporal sequence or the first ablation scan dataset 22 generated by anatomical scanner 20. The temporal sequence of eight (8) ablation scan datasets $22_{f1}$-$22_{f8}$ are registered to the coordinate system 60, whereby a temporal pixel intensity of each pixel 23 is aligned for processing by ablation probability model 32.

In practice, spatial mapper 31 may perform the spatial alignment using image registration technique(s) as known in the art of the present disclosure, which may be augmented with user input and which may be improved with mechanical control of anatomical scanner 20 (e.g., fixation of an ultrasound probe) and/or with respiratory motion gating technique(s) as known in the art as known in the art of the present disclosure.

Also in practice, spatial mapper 31 may augmented with a spatial tracking system (or an active or a passive mechanical holder) for anatomical scanner 20 (FIG. 1), thus preventing or compensating for motion of for anatomical scanner 20, which leaves remaining physiological tissue motion to be corrected using image-based methods. The spatial tracking system may also utilized by spatial mapper 31 to maintain a constant imaging field-of-view by providing feedback if anatomical scanner 20 is moved from an initial baseline imaging position.

Further in practice, a buffer size is dependent upon a frame rate of anatomical scanner 20 and may be regulated within a size range covering to a time span between one (1) second and one (1) minute.

Referring back to FIG. 2, during a stage S54 of flowchart 50, ablation probability model 32 is trained to render a pixel ablation probability for each pixel of an ablation scan image 42 (FIG. 1) illustrative of a static anatomical ablation. To this end, ablation probability model 32 retrieves the temporal sequence of spatially aligned ablation scan datasets 37 from the buffer to render a pixel ablation probability for each pixel of an ablation scan image 42 corresponding to an ablation scan dataset inclusive or related to the temporal sequence of spatially aligned ablation scan datasets 37.

In practice, ablation probability model 32 is any statistical analytical tool trained for estimating a probability of which area(s) of ablation scan image 42 are ablation area(s) on the basis of a temporal sequence of ablation scan images 42. The training of ablation probability model 32 may be trained from clinical data or simulated data to match the observed ablation behavior of tissue in general or in different tissue types. Alternatively or concurrently, ablation probability model 32 may be trained with different adaptations to the tissue type being ablated, different adaptations to the ablation electrode and/or different adaptations to the type of anatomical scanner 20.

In one embodiment, ablation probability model 32 defines a set of rules that describe how likely a given image pixel is part of an ablation area of ablation scan image 42, given a time history of image intensities at that pixel and at a neighborhood of pixels within N pixels around the pixel, N≥1. For this embodiment, FIG. 4 illustrates a flowchart 70 representative of one embodiment of an ablation probability model application method of the present disclosure.

Figure 4:
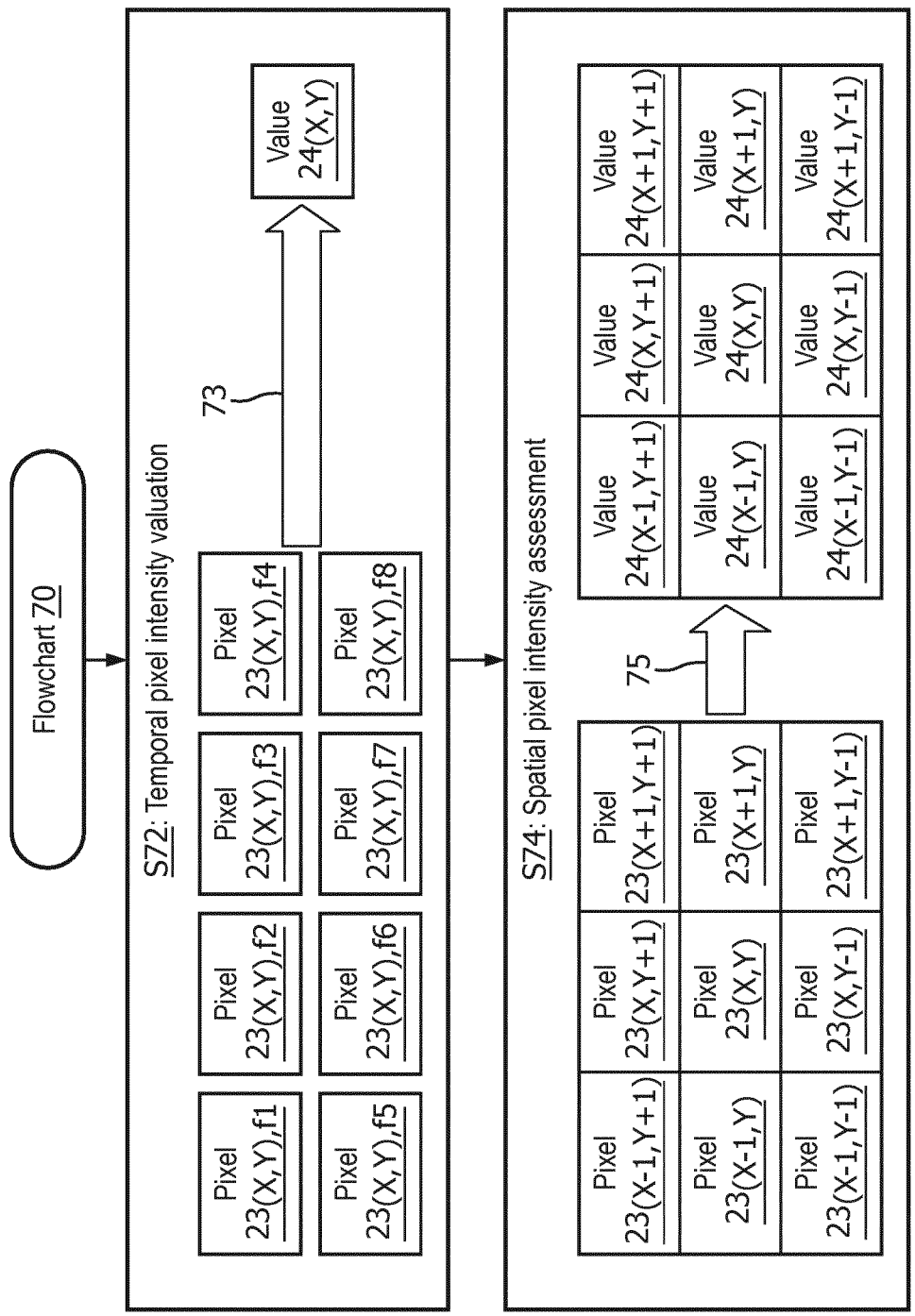
FIG. 4 illustrates an exemplary embodiment of a flowchart representative of a ablation probability model application method in accordance with various aspects of the present disclosure.
Figure 4:
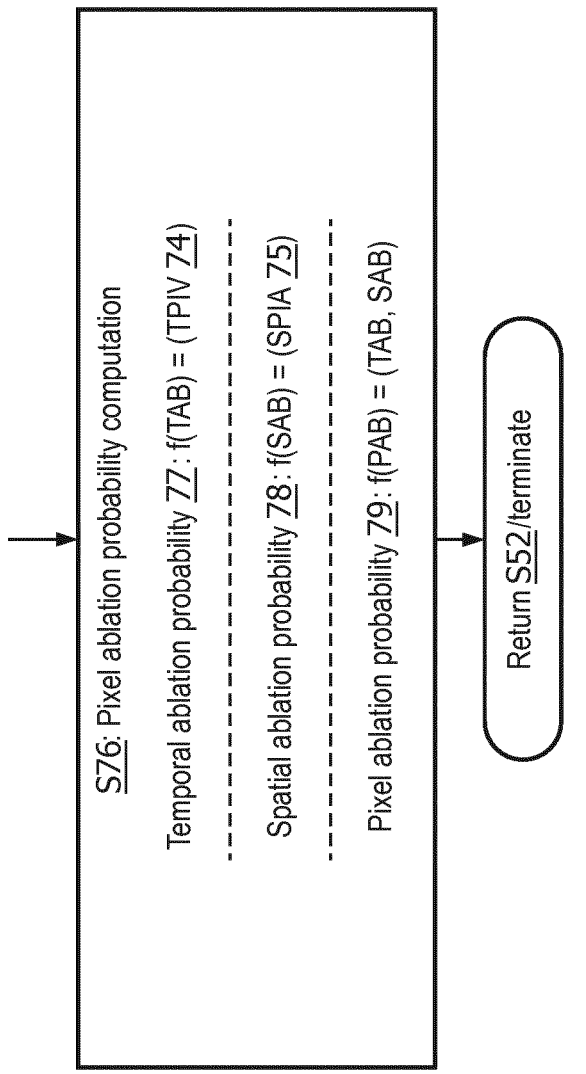

Referring to FIG. 4, a stage S72 of flowchart 70 encompasses ablation probability model 32 executing a valuation 73 of a temporal pixel intensity $24_{(X,Y)}$ of each pixel $23_{(X,Y)}$ of the temporal sequence of spatially aligned ablation scan datasets 37. For example, for ultrasound shear-wave elastography, each pixel of an ablation scan dataset 37 will have an intensity ranging between a blue colored intensity of ten (10) indicative of a unablated tissue stiffness, an unablated tissue density or an un-ablated tissue temperature and a red colored intensity of fifth (50) indicative of a fully ablated tissue stiffness, a fully ablated tissue density or a fully ablated tissue temperature.

In one embodiment of stage S72, the temporal pixel intensity $24_{(X,Y)}$ is an intensity average of the temporal pixel intensity of each pixel $23_{(X,Y)}$ of the temporal sequence of spatially aligned ablation scan datasets 37.

In a second embodiment of stage S72, the temporal pixel intensity $24_{(X,Y)}$ is a median intensity value of the temporal pixel intensity of each pixel $23_{(X,Y)}$ of the temporal sequence of spatially aligned ablation scan datasets 37.

In a third embodiment of stage S72, the temporal pixel intensity $24_{(X,Y)}$ is a maximum intensity value of the temporal pixel intensity of each pixel $23_{(X,Y)}$ of the temporal sequence of spatially aligned ablation scan datasets 37.

In a fourth embodiment of stage S72, the temporal pixel intensity $24_{(X,Y)}$ is a minimum intensity value of the temporal pixel intensity of each pixel $23_{(X,Y)}$ of the temporal sequence of spatially aligned ablation scan datasets 37.

In a fifth embodiment of stage S72, the temporal pixel intensity $24_{(X,Y)}$ is an intensity value derived from a standard deviation of the temporal pixel intensity of each pixel $23_{(X,Y)}$ of the temporal sequence of spatially aligned ablation scan datasets 37.

Still referring to FIG. 4, a stage S74 of flowchart 70 encompasses ablation probability model 32 executing as assessment 75 of temporal pixel intensity 24 of a spatial neighborhood of each pixel 23.

In practice, a spatial neighborhood of each pixel 23 is dependent upon an (X,Y) position of a given pixel 23 and the number of contiguous pixels 23, which consists of pixels 23 adjacent the given pixel 23.

For example, eight (8) pixel $23_{(X-1,Y+1)}$, pixel $23_{(X,Y+1)}$, pixel $23_{(X,Y+1)}$, pixel $23_{(X-1,Y)}$, pixel $23_{(X+1,Y)}$, pixel $23_{(X-1,Y-1)}$, pixel $23_{(X,Y-1)}$ and pixel $23_{(X+1,Y-1)}$ encircling a given pixel $23_{(X,Y)}$ are shown. One or more of these contiguous pixels 23 may be included within spatial neighborhood of the pixel $23_{(X,Y)}$. Additionally, one or more pixels (not shown) contiguous with the eight (8) pixels 23 and not contiguous with pixel $23_{(X,Y)}$ may be included within the spatial neighborhood of the pixel $23_{(X,Y)}$.

Upon a delineation of the spatial neighborhood of the pixel $23_{(X,Y)}$, the assessment 75 encompasses a grouping of the temporal pixel intensities 24 of the pixels 23.

Still referring to FIG. 4, a stage S76 of flowchart 70 encompasses ablation probability model 32 computing a temporal ablation probability 77, a spatial ablation probability 78 and a pixel ablation probability 79 in accordance with trained probability rules.

The probability rule(s) for temporal ablation probability 77 provide a preliminary estimation of a probability a given pixel $23_{(X,Y)}$ represents ablated tissue as a function of temporal pixel intensity valuation of the given pixel $23_{(X,Y)}$ during stage S72.

The probability rule(s) for spatial ablation probability 78 provide a supplemental estimation of a probability a given pixel $23_{(X,Y)}$ represents ablated tissue as a function of spatial pixel intensity assessment of the given pixel $23_{(X,Y)}$ during stage S74.

The probability rule(s) for pixel ablation probability 79 provide a final estimation of a probability a given pixel $23_{(X,Y)}$ represents ablated tissue as a function of both the temporal ablation probability 77 and the spatial ablation probability 78 for the given pixel $23_{(X,Y)}$.

Figure 5:
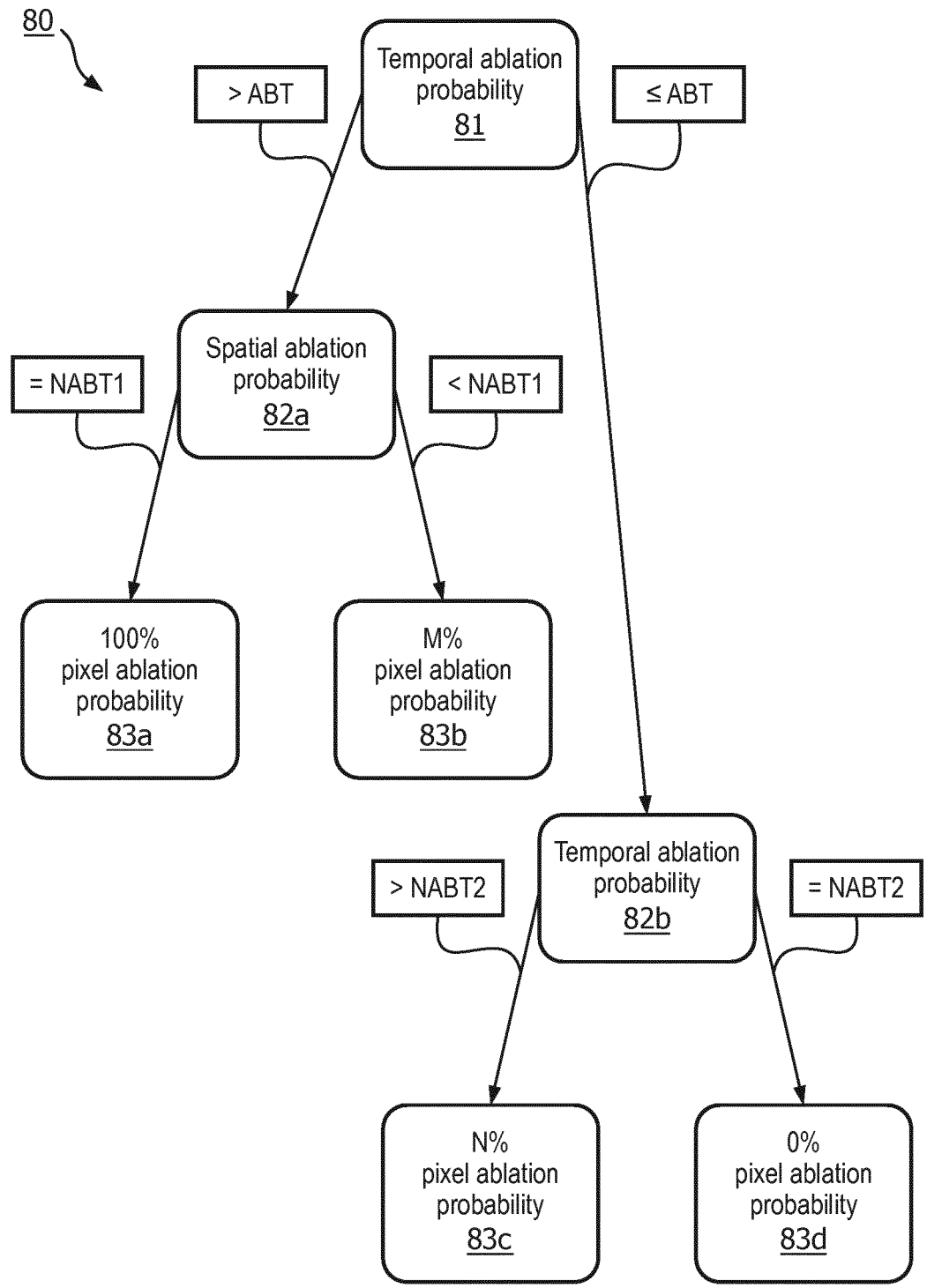
FIG. 5 illustrates an exemplary embodiment of a probabilistic decision tree in accordance with various aspects of the present disclosure.

In one embodiment, a probabilistic decision tree 80 as shown in FIG. 5 implements probabilistic rules for ablation probabilities 77-79.

Referring to FIG. 5, a node 81 compares a temporal pixel intensity valuation $24_{(X,Y)}$ of the given pixel $23_{(X,Y)}$ to an ablation intensity threshold ABT indicative of an ablated tissue stiffness, an ablated tissue density or an ablated tissue temperature (e.g., 48 for ultrasound shear-wave elastography).

If, at node 81, the temporal pixel intensity valuation $24_{(X,Y)}$ of the given pixel $23_{(X,Y)}$ is greater than the ablation intensity threshold ABT, then a node 82a determines if a number of neighbor pixels for the given pixel $23_{(X,Y)}$ equals a neighborhood ablation threshold NABT1. For example, neighborhood ablation threshold NABT1 is 100% of the neighboring pixels having a temporal pixel intensity valuation 24 greater than the ablation intensity threshold ABT.

If, at node 82a, the number of neighbor pixels for the given pixel $23_{(X,Y)}$ equals the neighborhood ablation threshold NABT1, then a node 83*a* deems the given pixel 23$_{(X,Y)}$ represents a 100% pixel ablation probability of ablated tissue.

If, at node 82*a*, the number of neighbor pixels for the given pixel 23$_{(X,Y)}$ is less than the neighborhood ablation threshold NABT1, then a node 83*b* deems the given pixel 23$_{(X,Y)}$ represents a M % pixel ablation probability of ablated tissue, M %≥50% and M %<100% dependent upon the temporal pixel intensity valuation 24 of all relevant pixels.

Conversely, if, at node 81, the temporal pixel intensity valuation 24$_{(X,Y)}$ of the given pixel 23$_{(X,Y)}$ is equal to or less than the ablation intensity threshold ABT, then a node 82*b* determines if a number of neighbor pixels for the given pixel 23$_{(X,Y)}$ equals a neighborhood ablation threshold NABT2. For example, neighborhood ablation threshold NAB2 is 0% of the neighboring pixels having a temporal pixel intensity valuation 24 greater than the ablation intensity threshold ABT.

If, at node 82*b*, the number of neighbor pixels for the given pixel 23$_{(X,Y)}$ is greater than the neighborhood ablation threshold NABT2, then a node 83*c* deems the given pixel 23$_{(X,Y)}$ represents a N % pixel ablation probability of ablated tissue, N %≥0% and N %<100% dependent upon the temporal pixel intensity valuation 24 of all relevant pixels.

If, at node 82*b*, the number of neighbors pixels for the given pixel 23$_{(X,Y)}$ equals the neighborhood ablation threshold NABT2, then a node 83*d* then a node 83*a* deems the given pixel 23$_{(X,Y)}$ represents a 0% pixel ablation probability of ablated tissue (i.e., un-ablated tissue).

To reach a specific % probability of ablated tissue, nodes 83*b* and nodes 83*c* may implement additional probability rules.

For example, a probability rule of node 83*c* may consider the pixel ablation probability of the given pixel 23$_{(X,Y)}$ to be ablated to 50% if the given pixel 23$_{(X,Y)}$ is adjacent to neighbor pixels of 100% pixel ablation probability and temporal pixel intensity valuation 24$_{(X,Y)}$ of the given pixel 23$_{(X,Y)}$ is larger than 80% of the ablation intensity threshold ABT.

By further example, a probability rule of node 83*c* may increase the pixel ablation probability of the given pixel 23$_{(X,Y)}$ to be ablated if the given pixel 23$_{(X,Y)}$ is adjacent to neighbor pixels of 100% pixel ablation probability and temporal pixel intensity valuation 24$_{(X,Y)}$ of the given pixel 23$_{(X,Y)}$ is larger than 90% of the ablation intensity threshold ABT.

By further example, a probability rule of node 83*c* may decrease the pixel ablation probability of the given pixel 23$_{(X,Y)}$ to be ablated if the given pixel 23$_{(X,Y)}$ is adjacent to neighbor pixels less than 100% pixel ablation probability and greater than 0% pixel ablation intensity, and temporal pixel intensity valuation 24$_{(X,Y)}$ of the given pixel 23$_{(X,Y)}$ is less than 80% of the ablation intensity threshold ABT.

In practice, probabilistic decision trees of the present disclosure may be defined with different adaptations to the tissue type being ablated, different adaptations to the ablation electrode and/or different adaptations to anatomical scanner 20.

In one embodiment, the threshold values and the pixel ablation probabilities may be calibrated based on test ablations in different tissue types.

In a second embodiment, a spatio-temporal model of the expected development of an ablation area (e.g. derived from finite element modelling) may be integrated by fitting ablation probability model 32 to the time history of ablation scan images. The probability of ablation at a given pixel 23$_{(X,Y)}$ may be defined as a combination of the image-derived probabilities combined with a quality metric (e.g., the DICE coefficient) of the model fit in the vicinity of given pixel 23$_{(X,Y)}$.

In a third embodiment, a spatio-temporal model of the expected development of an ablation area may be used to determine the threshold values in ablation probability model 32, by matching the computed ablation area in the early phase of the ablation to the image values obtained during those time points.

In a fourth embodiment, the threshold values and the pixel ablation probabilities may be learned with machine learning techniques (e.g., convolutional neural networks), by training the ablation probability model 32 with sufficient controlled experiments (with ground truth validation of the ablation zone with a reference imaging modality) or simulations of ablations imaged with the given imaging modality.

Referring back to FIG. 2, during a stage S54 of flowchart 50, image data generator 33 is configured to generate image data representative of the pixel ablation probability of each pixel as rendered by the ablation probability model 32 during stage S54.

In practice, image data generator 33 assigns a distinctive color level to each pixel with a 100% pixel ablation probability (e.g., white) and a distinctive color level to each pixel with a 0% pixel ablation probability (e.g., black). All other pixel(s) will have the same distinctive color level as all pixel(s) with a 0% pixel ablation probability or have a grey-scale color dependent upon the associated pixel ablation probability.

Also in practice, image data generator 33 may generate an ablation probability image dataset 34 whereby display processor 40 may generate a black/white or greyscale ablation probability image 43. The ablation probability image dataset 34 represents the contour(s) of ablation area(s) at a specific probability level (e.g., 100%) in a probability map.

Figure 6A:
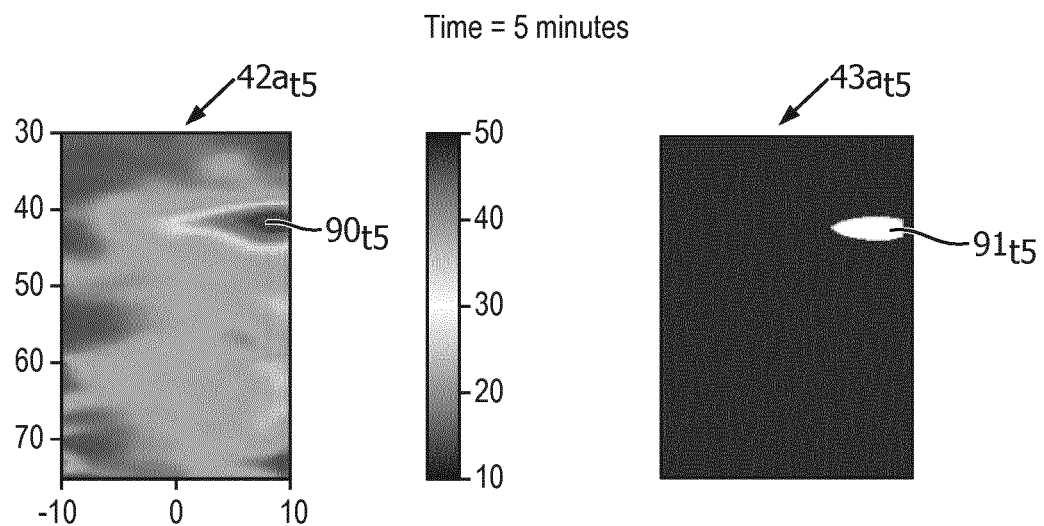
FIGS. 6A-6D illustrate an exemplary generation of a temporal sequence of ablation scan images and ablation probability images in accordance with various aspects of the present disclosure.
Figure 6B:
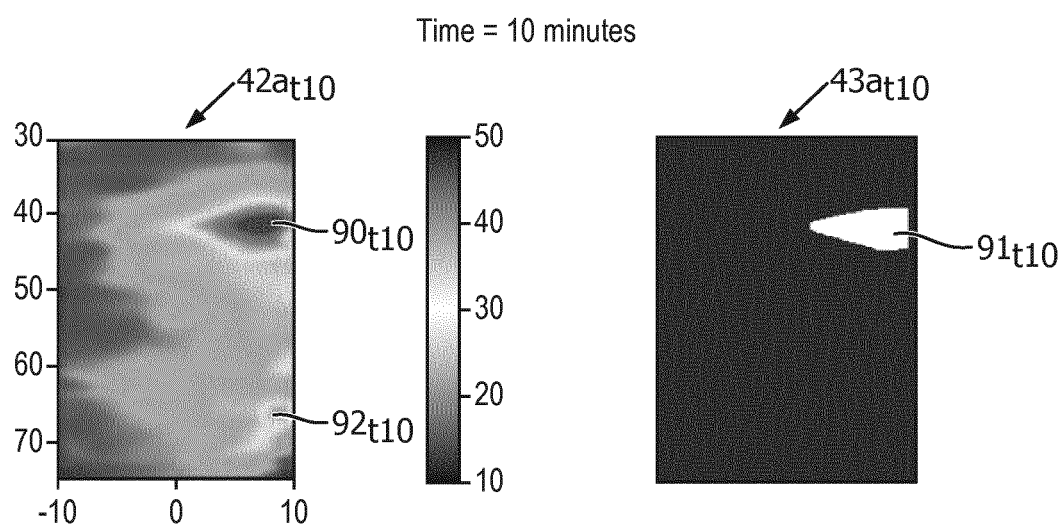
Figure 6C:
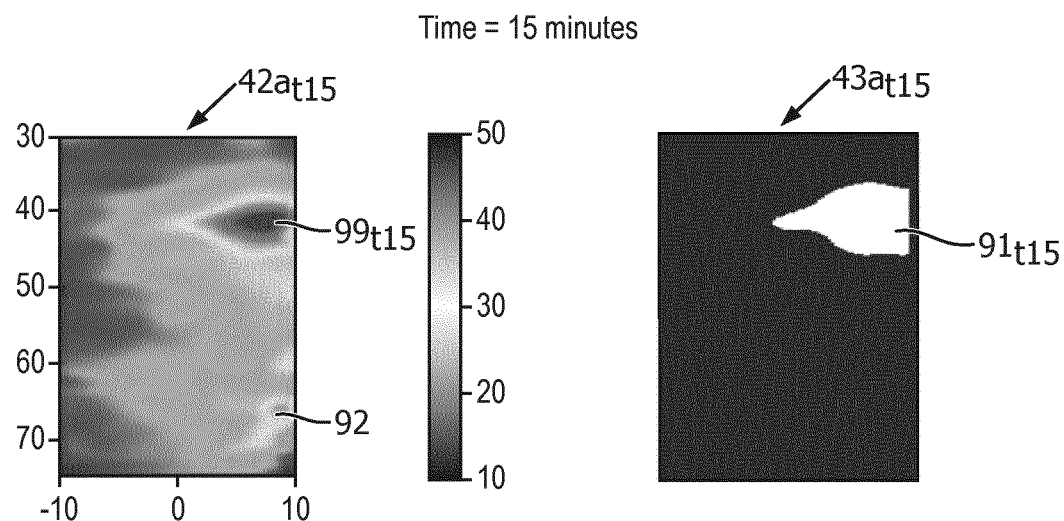
Figure 6D:
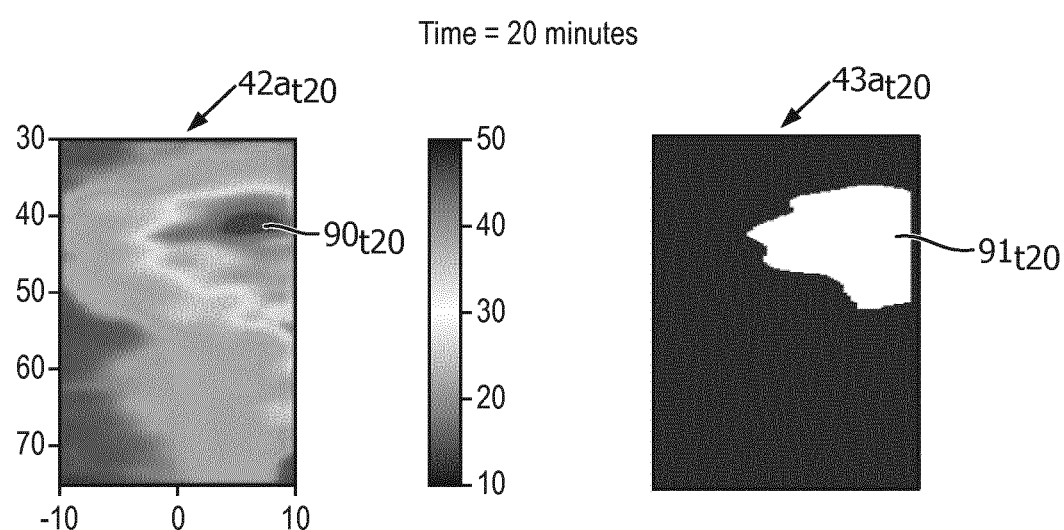

For example, FIGS. 6A-6D illustrate a sequence of ultrasound shear-wave elastography images 42*a* having an ablation area 90 and corresponding ablation probability images 43*a* having ablation area 91 at t=five (5) minutes as shown in FIG. 6A, t=ten (10) minutes as shown in FIG. 6B, t=fifteen (15) minutes as shown in FIG. 6C and t=twenty (20) minutes as shown in FIG. 6D.

Of importance to note with reference to FIGS. 6A-6D is how the ablation probability model 32 defines the increasing ablation 90 ultrasound shear-wave elastography images 42*a* without including the artefact 92 that temporarily appears below the ablation area 90 at t=ten (10) minutes and t=fifteen (15) minutes, but which disappears again at t=twenty (20) minutes after imaging conditions improve.

Referring back to FIG. 2, alternatively or concurrently, image data generator 33 may generate an ablation probability anatomical overlay dataset 35 whereby display processor 40 may generate an overlay of probable ablation area(s) on an anatomical scan image 44 (e.g., a B-mode ultrasound image). The ablation probability image overlay dataset 35 represent a contour of ablation area at a specific probability level (e.g., 100%) in an anatomical scan image.

Figure 7:
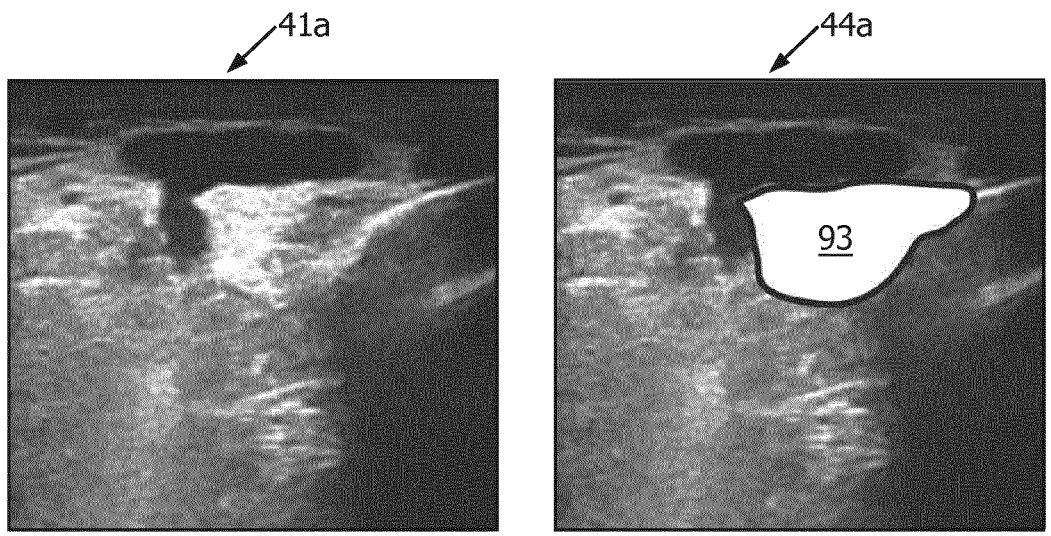
FIG. 7 illustrates an exemplary generation of an anatomical scan image and an ablation probability anatomical scan image in accordance with various aspects of the present disclosure.
Figure 8:
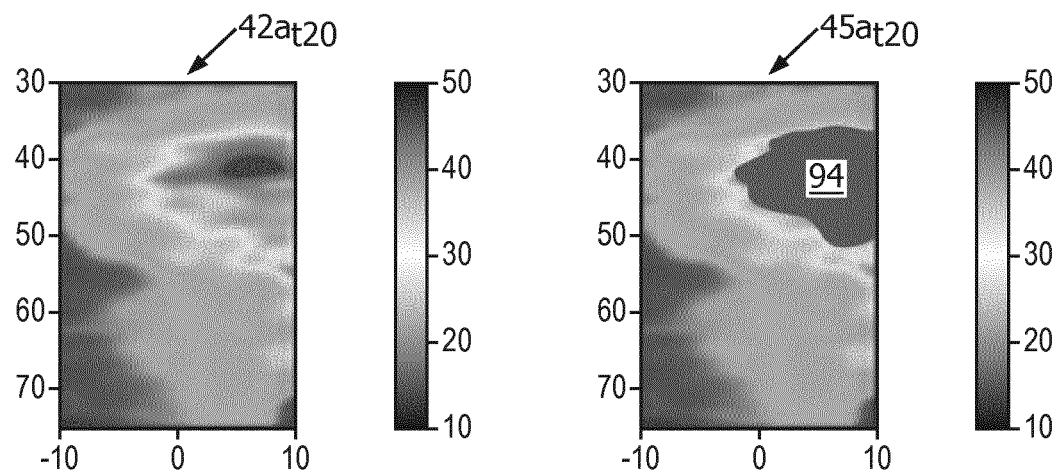
FIG. 8 illustrates an exemplary generation of an ablation scan image and an ablation probability ablation scan image in accordance with various aspects of the present disclosure.

For example, FIG. 7 illustrates an anatomical image 41*a* and anatomical image 44*a* having an ablation overlay 93 rendered by ablation probability model 32.

Referring back to FIG. 2, alternatively or concurrently, image data generator 33 may generate an ablation probability anatomical overlay dataset 36 whereby display processor 40 may generate an overlay of probable ablation area(s) on an anatomical scan image 44. The ablation probability image overlay dataset 36 represent a contour of ablation area at a specific probability level (e.g., 100%) in an ablation scan image.

For example, FIG. 7 illustrates an ablation image 42a and ablation image 45a having a ablation overlay 92 rendered by ablation probability model 32.

Referring back to FIG. 2, flowchart 50 is performed in a loop during the ablation procedure.

In practice, spatial mapper 31 operated in a mode controlling an updating frequency of the ablation probability of each pixel.

In one embodiment, spatial mapper 31 operates under a newest ablation scan dataset 32 in buffer/oldest ablation scan dataset 32 out of buffer mode whereby each scan of ablated anatomical region 10 results in an updated ablation probability of each pixel.

In a second embodiment, spatial mapper 31 operates under clear buffer/fill buffer mode whereby each Nth scan of ablated anatomical region 10 results in an updated ablation probability of each pixel.

Figure 9:
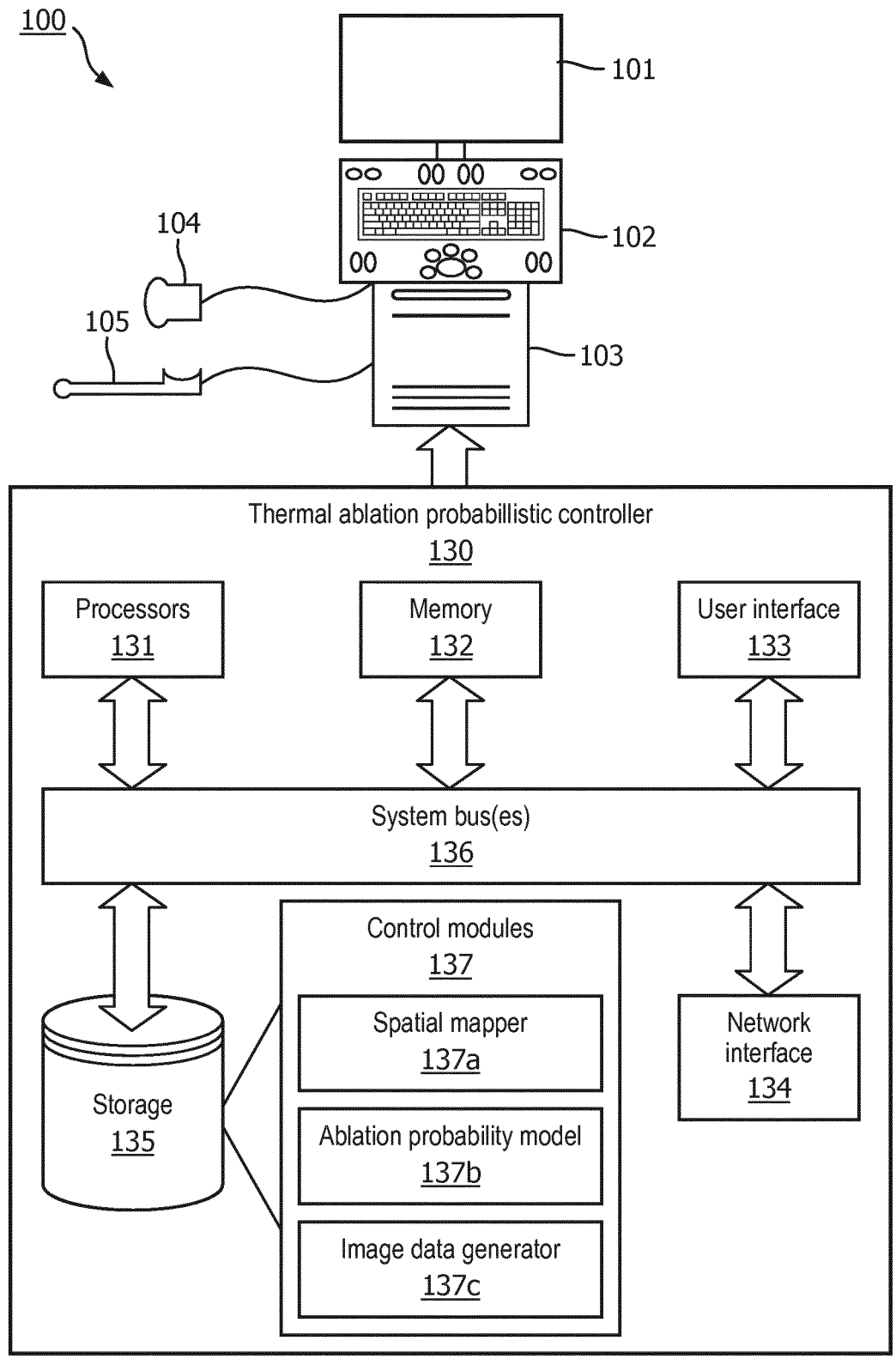
FIG. 9 illustrates exemplary embodiments of an image scanner and a thermal ablation probability controller in accordance with various aspects of the present disclosure.

To facilitate a further understanding of the various inventions of the present disclosure, the following description of FIG. 9 teaches an exemplary embodiment of a thermal ablation probability controller of the present disclosure. From this description, those having ordinary skill in the art will appreciate how to apply various aspects of the present disclosure for making and using additional embodiments of thermal ablation probability controller of the present disclosure.

Referring to FIG. 9, a thermal ablation probability controller 130 includes one or more processor(s) 131, memory 132, a user interface 133, a network interface 134, and a storage 135 interconnected via one or more system buses 136.

Each processor 131 may be any hardware device, as known in the art of the present disclosure or hereinafter conceived, capable of executing instructions stored in memory 132 or storage or otherwise processing data. In a non-limiting example, the processor(s) 131 may include a microprocessor, field programmable gate array (FPGA), application-specific integrated circuit (ASIC), or other similar devices.

The memory 132 may include various memories, as known in the art of the present disclosure or hereinafter conceived, including, but not limited to, L1, L2, or L3 cache or system memory. In a non-limiting example, the memory 132 may include static random access memory (SRAM), dynamic RAM (DRAM), flash memory, read only memory (ROM), or other similar memory devices.

The user interface 133 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 134.

The network interface 134 may include one or more devices, as known in the art of the present disclosure or hereinafter conceived, for enabling communication with other hardware devices. In a non-limiting example, the network interface 134 may include a network interface card (NIC) configured to communicate according to the Ethernet protocol. Additionally, the network interface 134 may implement a TCP/IP stack for communication according to the TCP/IP protocols. Various alternative or additional hardware or configurations for the network interface 134 will be apparent.

The storage 135 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 135 may store instructions for execution by the processor(s) 131 or data upon with the processor(s) 131 may operate. For example, the storage 135 may store a base operating system for controlling various basic operations of the hardware. The storage 135 also stores application modules in the form of executable software/firmware for implementing the various functions of the controller 130a as previously described in the present disclosure including, but not limited to, a spatial mapper 137a, an ablation probability model 137b and an image data generator 137c as previously described in the present disclosure.

Controller 130 is installed within a stand-alone workstation 100 employing a monitor 101, a keyboard 102, a computer 103 and ultrasound probes 104 and 105. A display processor (not shown) and a scanning processor (not shown) are also installed within computer 103. Alternatively, controller 130 may be installed within a server whereby controller is accessible via a client workstation, or a mobile device (e.g., a tablet).

Referring to FIGS. 1-9, those having ordinary skill in the art of the present disclosure will appreciate numerous benefits of the inventions of the present disclosure including, but not limited to, a probabilistic approach to identify ablation area(s) based on the observation and tracking of individual ablation monitoring images over time.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A thermal ablation probabilistic controller, comprising:
a memory including an ablation probability model trained to render a pixel ablation probability for at least some pixels of an ablation scan image illustrative of a static anatomical ablation; and
at least one processor in communication with the memory, wherein the at least one processor is configured to:
spatially align a temporal sequence of ablation scan datasets representative of a dynamic anatomical ablation; and
apply the ablation probability model to the spatial alignment of the temporal sequence of ablation scan datasets to render the pixel ablation probability for at least some pixels of the ablation scan image illustrative of the static anatomical ablation.

2. The thermal ablation probabilistic controller of claim 1, wherein the application of the ablation probability model to the spatial alignment of the temporal sequence of ablation scan datasets further includes the at least one processor configured to:
derive a temporal pixel intensity of a pixel of the ablation scan image illustrative of the static anatomical ablation from the spatial alignment of the temporal sequence of ablation scan datasets;
derive a temporal pixel intensity of at least one neighboring pixel of the ablation scan image illustrative of the static anatomical ablation from the spatial alignment of the temporal sequence of ablation scan datasets; and
apply an ablation probability rule to the temporal pixel intensities of the pixel and the at least one neighboring pixel to render the pixel ablation probability of the pixel.

3. The thermal ablation probabilistic controller of claim 1, wherein the temporal pixel intensity valuation of at least some pixels of the temporal sequence of ablation scan datasets is one of:
an intensity average of the temporal sequence of at least some pixels of the spatial alignment of the temporal sequence of ablation scan datasets;
a median intensity value of the temporal sequence of at least some pixels of the spatial alignment of the temporal sequence of ablation scan datasets;
a maximum intensity value of the temporal sequence of at least some pixels of the spatial alignment of the temporal sequence of ablation scan datasets;
a minimum intensity value of the temporal sequence of at least some pixels of the spatial alignment of the temporal sequence of ablation scan datasets; and
an intensity value derived from a standard deviation of the temporal sequence of at least some pixels of the spatial alignment of the temporal sequence of ablation scan datasets.

4. The thermal ablation probabilistic controller of claim 1, wherein the at least one processor is further configured to at least one of:
generate an ablation probability image derived from the pixel ablation probability for at least some pixels of the ablation scan image illustrative of the static anatomical ablation;
generate an ablation probability anatomical scan image derived from an anatomical image of the static anatomical ablation and further derived from the pixel ablation probability for at least some pixels of the ablation scan image illustrative of the static anatomical ablation; and
generate an ablation probability ablation scan image derived from the ablation scan image illustrative of the static anatomical ablation and further derived from the pixel ablation probability for at least some pixels of the ablation scan image illustrative of the static anatomical ablation.

5. The thermal ablation probabilistic controller of claim 1, wherein an intensity value of at least some pixels of the temporal sequence of ablation scan datasets is representative of one of an anatomical stiffness, an anatomical density or an anatomical temperature.

6. The thermal ablation probabilistic controller of claim 1, wherein the application of the ablation probability model to the spatial alignment of the temporal sequence of ablation scan datasets includes the at least one processor configured to:
execute a temporal pixel intensity valuation, by the ablation probability model, of a temporal sequence of at least some pixels of the spatial alignment of the temporal sequence of ablation scan datasets.

7. The thermal ablation probabilistic controller of claim 6, wherein the application of the ablation probability model to the spatial alignment of the temporal sequence of ablation scan datasets further the at least one processor configured to:
execute a spatial pixel intensity assessment, by the ablation probability model, of the temporal pixel intensity valuation of one or each of at least one neighboring pixel of the spatially alignment of the temporal sequence of ablation scan datasets.

8. The thermal ablation probabilistic controller of claim 7, wherein the application of the ablation probability model to the spatial alignment of the temporal sequence of ablation scan datasets further the at least one processor configured to:

apply, by the ablation probability model, at least one ablation probability rule to the temporal pixel intensity valuation and the spatial pixel intensity assessment the pixel ablation probability for at least some pixels of the ablation scan image illustrative of the static anatomical ablation, wherein the at least one ablation probability rules are based on a comparison of the temporal pixel intensity valuations of the pixel and the at least one neighboring pixel to an ablation threshold.

9. A non-transitory machine-readable storage medium encoded with instructions for execution by at least one processor of an ablation probability model trained to render a pixel ablation probability for at least some pixels of an ablation scan datasets representative of a static anatomical ablation, the non-transitory machine-readable storage medium comprising instructions to:

spatially align a temporal sequence of ablation scan datasets representative of a dynamic anatomical ablation; and apply the ablation probability model to the spatial alignment of the temporal sequence of ablation scan datasets to render the pixel ablation probability for at least some pixels of the ablation scan image illustrative of the static anatomical ablation.

10. The non-transitory machine-readable storage medium of claim 9, wherein the application of the ablation probability model to the spatial alignment of the temporal sequence of ablation scan datasets includes instructions to:

derive a temporal pixel intensity of a pixel of the ablation scan image illustrative of the static anatomical ablation from the spatial alignment of the temporal sequence of ablation scan datasets;

derive a temporal pixel intensity of at least one neighboring pixel of the ablation scan image illustrative of the static anatomical ablation from the spatial alignment of the temporal sequence of ablation scan datasets; and apply an ablation probability rule to the temporal pixel intensity of the pixel and the temporal pixel intensity of at least one neighboring pixel to render the pixel ablation probability of the pixel.

11. The non-transitory machine-readable storage medium of claim 9, further comprising instructions to at least one of:

generate an ablation probability image derived from the pixel ablation probability for at least some pixels of the ablation scan image illustrative of the static anatomical ablation;

generate an ablation probability anatomical scan image derived from an anatomical image of the static anatomical ablation and further derived from the pixel ablation probability for at least some pixels of the ablation scan image illustrative of the static anatomical ablation; and generate an ablation probability ablation scan image derived from the ablation scan image illustrative of the static anatomical ablation and further derived from the pixel ablation probability for at least some pixels of the ablation scan image illustrative of the static anatomical ablation.

12. The non-transitory machine-readable storage medium of claim 9, wherein the instructions to apply the ablation probability model the spatial alignment of the temporal sequence of ablation scan datasets includes instructions to:

execute, by the ablation probability model, a temporal pixel intensity valuation of a temporal sequence of at least some pixels of the spatially alignment of the temporal sequence of ablation scan datasets.

13. The non-transitory machine-readable storage medium of claim 12, wherein the temporal pixel intensity valuation of at least some pixels of the temporal sequence of ablation scan datasets is one of:

an intensity average of the temporal sequence of at least some pixels of the spatial alignment of the temporal sequence of ablation scan datasets;

a median intensity value of the temporal sequence of at least some pixels of the spatial alignment of the temporal sequence of ablation scan datasets;

a maximum intensity value of the temporal sequence of at least some pixels of the spatial alignment of the temporal sequence of ablation scan datasets;

a minimum intensity value of the temporal sequence of at least some pixels of the spatial alignment of the temporal sequence of ablation scan datasets; and an intensity value derived from a standard deviation of the temporal sequence of at least some pixels of the spatial alignment of the temporal sequence of ablation scan datasets.

14. The non-transitory machine-readable storage medium of claim 12, wherein the instructions to apply the ablation probability model the spatial alignment of the temporal sequence of ablation scan datasets further includes instructions to:

compute, by the ablation probability model, a spatial pixel intensity assessment of the temporal pixel intensity valuation of one or each of at least one neighboring pixel of the spatial alignment of the temporal sequence of ablation scan datasets.

15. The non-transitory machine-readable storage medium of claim 14, wherein the instructions to apply the ablation probability model the spatial alignment of the temporal sequence of ablation scan datasets further includes instructions to:

apply, by the ablation probability model, at least one ablation probability rule to the temporal pixel intensity valuation and the spatial pixel intensity assessment the pixel ablation probability for at least some pixels of the ablation scan image illustrative of the static anatomical ablation, wherein the at least one ablation probability rules are based on a comparison of the temporal pixel intensity valuations of the pixel and the at least one neighboring pixel to an ablation threshold.

16. A thermal ablation probabilistic method executable by a thermal ablation probabilistic controller including an ablation probability model trained to render a pixel ablation probability for at least some pixels of an ablation scan datasets representative of a static anatomical ablation, the thermal ablation probabilistic method comprising:

spatially aligning, by the thermal ablation probabilistic controller, a temporal sequence of ablation scan datasets representative of a dynamic anatomical ablation; and applying, by the thermal ablation probabilistic controller, the ablation probability model to the spatial alignment of the temporal sequence of ablation scan datasets to render the pixel ablation probability for at least some pixels of the ablation scan image illustrative of the static anatomical ablation.

17. The thermal ablation probabilistic method of claim 16, wherein the applying, by the thermal ablation probabilistic controller, of the ablation probability model to the spatial alignment of the temporal sequence of ablation scan datasets includes:

deriving a temporal pixel intensity of a pixel of the ablation scan image illustrative of the static anatomical ablation from the spatial alignment of the temporal sequence of ablation scan datasets;

deriving a temporal pixel intensity of at least one neighboring pixel of the ablation scan image illustrative of the static anatomical ablation from the spatial alignment of the temporal sequence of ablation scan datasets; and applying an ablation probability rule to the temporal pixel intensity of the pixel and the temporal pixel intensity of at least one neighboring pixel to render the pixel ablation probability of the pixel.

18. The thermal ablation probabilistic method of claim 16, wherein the applying, by the thermal ablation probabilistic controller, of the ablation probability model the spatial alignment of the temporal sequence of ablation scan datasets includes:

executing, by the ablation probability model, a temporal pixel intensity valuation of a temporal sequence of at least some pixels of the spatial alignment of the temporal sequence of ablation scan datasets; and executing, by the ablation probability model, a spatial pixel intensity of the temporal pixel intensity valuation of one or each of at least one neighboring pixel of at least some pixels the spatial alignment of the temporal sequence of ablation scan datasets.

19. The thermal ablation probabilistic method of claim 16, wherein the applying, by the thermal ablation probabilistic controller, of the ablation probability model the spatial alignment of the temporal sequence of ablation scan datasets further includes:

applying, by the ablation probability model, at least one probability rule to the temporal pixel intensity valuation and the spatial pixel intensity assessment to render the pixel ablation probability for at least some pixels of the ablation scan image illustrative of the static anatomical ablation, wherein the at least one ablation probability rules are based on a comparison of the temporal pixel intensity valuations of the pixel and the at least one neighboring pixel to an ablation threshold.

20. The thermal ablation probabilistic method of claim 16, further comprising at least one of:

generating an ablation probability image derived from the pixel ablation probability for at least some pixels of the ablation scan image illustrative of the static anatomical ablation;

generating an ablation probability anatomical scan image derived from an anatomical image of the static anatomical ablation and further derived from the pixel ablation probability for at least some pixels of the ablation scan image illustrative of the static anatomical ablation; and generating an ablation probability ablation scan image derived from the ablation scan image illustrative of the static anatomical ablation and further derived from the pixel ablation probability for at least some pixels of the ablation scan image illustrative of the static anatomical ablation.

* * * * *